United States Patent [19]

Livingston et al.

[11] Patent Number: 4,605,297

[45] Date of Patent: Aug. 12, 1986

[54] METHOD OF AND APPARATUS FOR CONTROLLING THE APPLICATION OF PROCESSING FLUID

[75] Inventors: James J. Livingston, Waltham; Duncan C. Sorli, Chelmsford, both of Mass.

[73] Assignee: Polaroid Corporation, Cambridge, Mass.

[21] Appl. No.: 685,403

[22] Filed: Dec. 24, 1984

[51] Int. Cl.$^4$ .............................................. G03D 9/00
[52] U.S. Cl. .................................... 354/303; 354/305; 354/317; 118/410; 118/683; 118/688; 222/58; 222/375
[58] Field of Search ............... 354/298, 317, 318, 324, 354/303, 305; 118/410, 411, 672, 683, 688, 694; 222/58, 63, 375

[56] References Cited

U.S. PATENT DOCUMENTS

| 2,435,719 | 10/1968 | Land et al. | 354/303 |
|---|---|---|---|
| 2,520,641 | 8/1950 | Land | 354/303 |
| 2,558,858 | 10/1968 | Land et al. | 354/303 |
| 2,563,343 | 10/1968 | Land | 354/303 |
| 2,719,789 | 11/1966 | Land et al. | 354/86 |
| 3,120,792 | 2/1964 | Erikson | 354/303 |
| 3,142,242 | 9/1984 | Cocco et al. | 354/310 |
| 3,453,138 | 3/1976 | Brown et al. | 354/302 |
| 3,621,772 | 11/1971 | Bogue | 354/317 |
| 3,644,024 | 2/1972 | Downey | 352/130 |
| 3,648,584 | 4/1969 | Chen et al. | 156/522 |
| 3,747,813 | 7/1973 | Downey | 222/541 |
| 4,148,274 | 4/1979 | Stievenart et al. | 118/683 |
| 4,225,638 | 9/1980 | Waugh | 118/410 |
| 4,526,455 | 7/1985 | Livingston | 354/317 |
| 4,526,456 | 7/1985 | Livingston | 354/317 |
| 4,531,820 | 7/1985 | Peterson | 354/234.1 |

Primary Examiner—A. A. Mathews
Attorney, Agent, or Firm—Leslie J. Payne

[57] ABSTRACT

A method of an apparatus for insuring application of a preselected amount of processing fluid to photographic film material are disclosed. A weight sensing device weighs a container of the fluid and permits pumping of the fluid if there is an adequate amount of fluid contained in the container. A magnetic sensing arrangement also effects reversal of the pumping after a preselected length of material has had fluid applied thereto. At the completion of fluid application, the fluid is evacuated from the nozzle.

9 Claims, 2 Drawing Figures

METHOD OF AND APPARATUS FOR CONTROLLING THE APPLICATION OF PROCESSING FLUID

BACKGROUND OF THE INVENTION

The present invention relates generally to a method of and apparatus for controlling the application of processing fluid of the type for processing photographic film. More specifically, it is directed to a method of and apparatus for insuring that a preselected length of film is processed by a predetermined quantity of preselected and easily oxidizable processing fluid, while minimizing the detrimental effects of oxidation of such fluid on processing operations.

A variety of photographic processes of the self-developing type broadly involve the application of a viscous liquid reagent across exposed photographic sheet material. Ordinarily in these processes a photosensitive sheet is first exposed and then later superposed with respect to a second sheet. The two superposed sheets are then moved between a pair of juxtaposed pressure applying members. Prior to the sheets moving between the pressure applying members processing fluid is introduced to and between them. The pressure applying members are constructed and arranged to spread the fluid in an approximately uniform layer over a desired exposed portion of one of the sheets. The spread of processing fluid initiates formation of visible images in one of the two sheets.

Significant problems can arise, however, with handling and distributing such a fluid. For example, the fluid is quickly oxidized upon exposure to air. Once oxidized the fluid hardens in the dispensing system and, therefore, subsequent accurate dispensing is impeded. The likelihood for hardening increases somewhat when the film processing operation is intermittent since there is a greater chance of contact with the ambient air.

Attempts have been made to effectively seal the pressurized fluid in the distribution lines particularly with valve systems that permit intermittent dispensing. Representative examples of such approaches are disclosed in the following commonly-assigned U.S. Pat. Nos. 2,435,719; 2,558,858; 2,563,343; 2,719,789; 3,210,792; 3,453,138; 3,142,242, and 3,648,584.

While, in general, such valve systems perform satisfactorily there remains nonetheless a problem in that hardening of even small amounts of fluid can hamper desired sliding movement of valve parts which contact the fluid. Stuck valves obviously hinder desired dispensing, but even worse increase the potential of exposed film portions being unprocessed or undesired flow of processing fluid contacting and contaminating other processing components.

In processing photographic film of the self-developing type, the fluid used should be matched chemically to the sensitivity of the film for optimum processing results. It becomes important, therefore, to have a system that permits each roll of film developed to be processed only by the chemically correct processing fluid. Moreover, it is desired to insure that an entire roll is processed with the correctly matched processing fluid in a manner easily handled by non-technical personnel.

SUMMARY OF THE INVENTION

In accordance with the present invention there is provided an apparatus for applying a coating of fluid initially retained in a container to an elongated section of a web of material. Included in the apparatus is a fluid dispensing nozzle and means for progressively advancing the web along a predetermined path into operative relationship with the nozzle. For receiving the container there is provided a weight sensing arrangement. For pumping the fluid from the container to the nozzle there is provided a pumping means including a pump and a fluid line operatively associated with both the pump and the nozzle. Such an apparatus includes means for enabling the pump to be rendered operable only when the weight sensing means senses a weight indicative that an amount of fluid retained in the container is sufficient to cover the entire elongated section of the web.

In an illustrated emodiment, the pump is a reversible type and includes means for automatically reversing the pump responsive to the entire length of the elongated section of the web having been coated with the fluid thereby effecting an evacuation of at least a substantial portion of the fluid line and the nozzle.

Among the other objects of the present invention are, therefore, the provision of an improved apparatus for applying a coating of fluid initially retained in a container to an elongated section of a photographic film material; the provision of a fluid applying apparatus wherein the processing fluid is pumped to a dispensing nozzle only when a weight sensing apparatus senses a weight indicative of an adequate amount of processing fluid; the provision of an apparatus wherein a pump for pumping the fluid is reversible and is operable to effect evacuation of the nozzle and a fluid delivery line responsive to an entire length of film having been coated; and the provision of a fluid dispensing method wherein a plurality of different rolls of exposed film are to be processed and the nozzle and source of fluid are disposable so that a new nozzle and source of fluid can be used for processing each new roll of film.

The above and other objects and further scope of applicablity of the present invention will become apparent from the detailed description to follow when taken in conjunction with the accompanying drawings wherein like parts are designated by like reference numerals throughout the several views.

DETAILED DESCRIPTION

Figure 1:
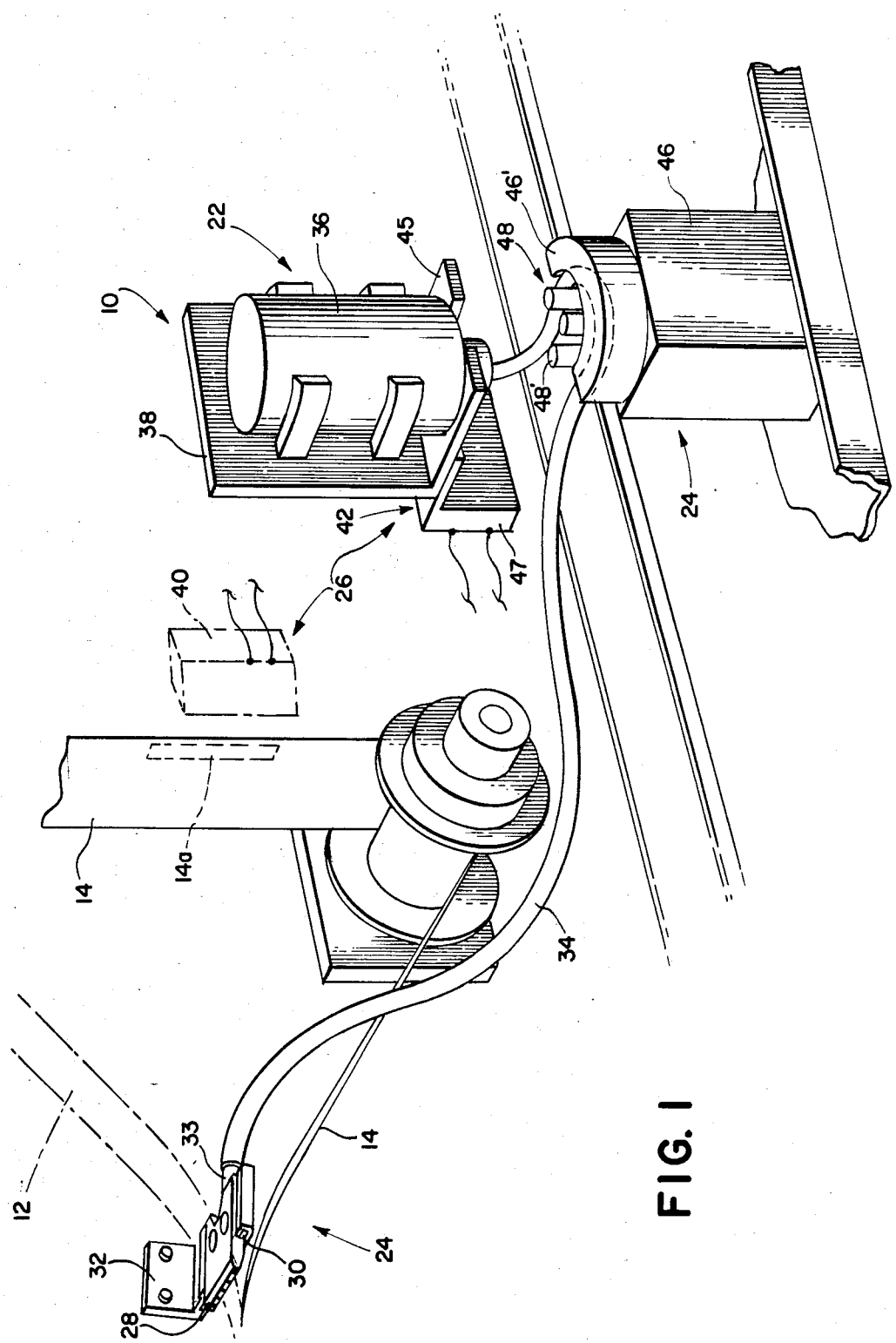
FIG. 1 is a perspective view showing part of the fluid dispensing apparatus of the present invention; and, FIG. 2 is a diagrammatic view in block diagram form showing the fluid dispensing apparatus of the present invention.
Figure 2:
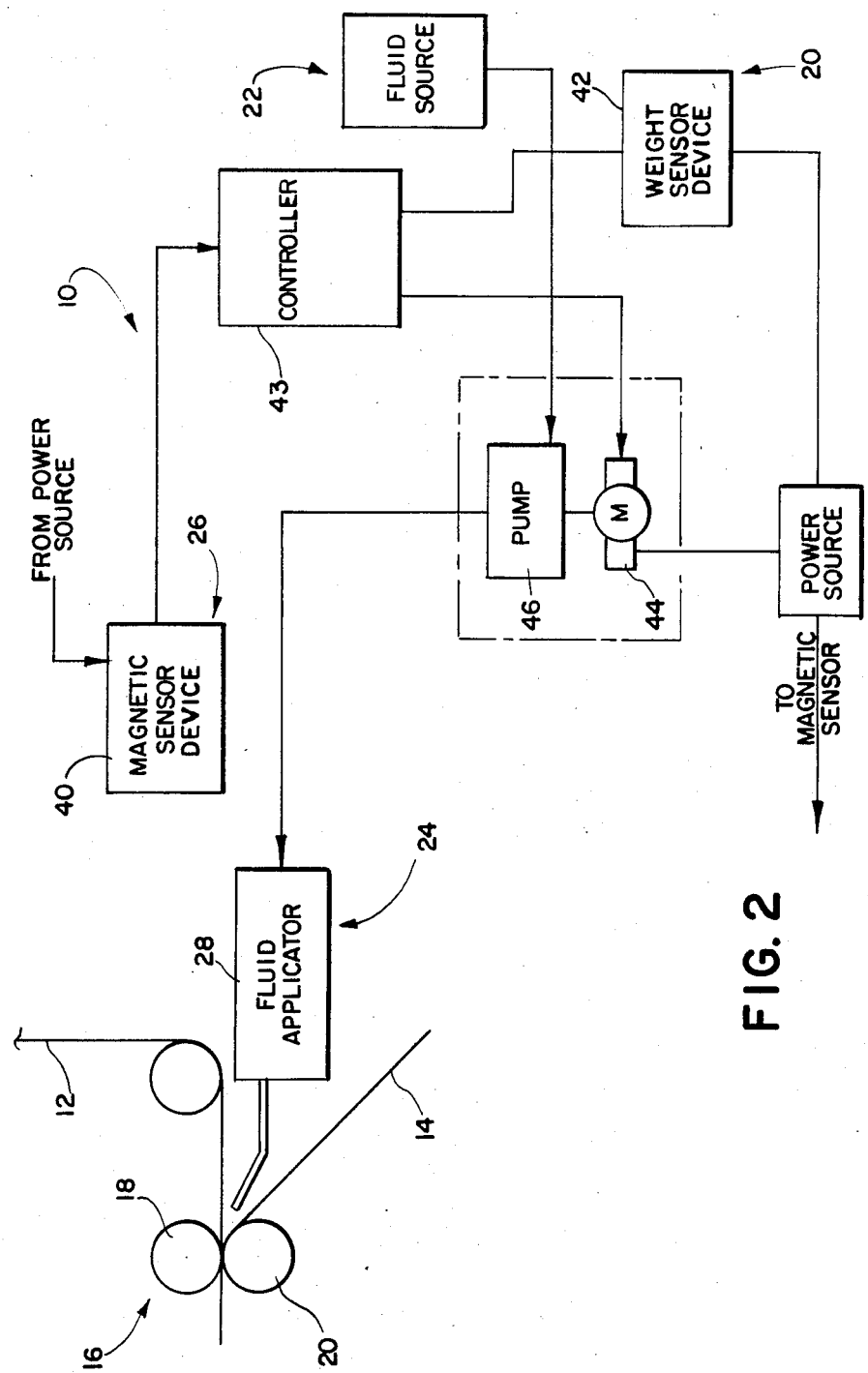

Reference is made to FIGS. 1 and 2 of the drawings for showing a system 10 for delivering processing fluid of the type for processing photographic film material of the instant developing type.

In this embodiment, the processing fluid is distributed to and between a pair of converging photographic type image-receiving and image-forming sheets 12 and 14; respectively, The sheets 12 and 14 are drawn along converging paths by a conventional type of processing assembly, indicated generally by reference number 16. Only a pair of pressure applying rollers 18 and 20 are shown. The processing assembly 16 does not form an aspect of this invention, thus a detailed description thereof has been dispensed with. Only those portions of the processing assembly 16 necessary for an understanding of the present invention will be described.

In this embodiment the photosensitive negative image-forming sheet 14 is of the type having a plurality of layers including a photosensitive layer, which has been photographically exposed previously in a camera, and which, of course, carries the latent images thereon. The positive or image-receiving sheet 12 is made of a flexible sheet material which is capable of supporting thereon a positive transfer print. To effect such a transfer from the negative to the positive, the processing fluid is spread between the sheets 12, 14 and the sheets are kept superposed for at least a preselected imbibition period. The processing fluid is a relatively viscous and easily oxidizable material.

Spreading of the processing fluid into a uniform layer is achieved by the rollers 18, 20 which have a predetermined gap set therebetween. As noted, the pressure applying rollers 18 and 20 facilitate not only superimposing of sheets 12,14 but spreading of such fluid to commence imbibition. It should be pointed out that subsequent to imbibition, the sheets 12 and 14 are stripped by means not shown and into forming part of the present invention. Although the present embodiment has disclosed that the visible images will be formed on the positive sheet 12, it is also contemplated by the present invention that the visible images may be formed in the negative sheet 14. In this regard, the sheet 12 would serve to spread the processing fluid.

The fluid applying apparatus or system 10 is arranged to essentially insure that there is a sufficient amount of processing fluid to process a preselected length of exposed image-forming sheet 14.

Essentially, the fluid applying system 10 comprises a fluid supply arrangement 22, fluid distribution assembly 24 and a fluid sensing assembly 26 for effecting control of the fluid dispensing.

Included in the fluid distribution assembly 24 is a fluid nozzle 28 which is removably mounted to the processing assembly 16 adjacent an area at which the sheets 12, 14 become superposed. A variety of fluid applicators can be used for dispensing purposes. However, in this embodiment, the nozzle 28 is disposable in the sense that it is intended to be thrown-away after a single roll of negative has been processed by the easily oxidizable fluid. Towards this end, it is provided with ribs 30 on its longitudinal sides which slidably cooperate with recesses (no shown) formed in a frame 32 of the processing assembly 16. An inlet end 33 of the nozzle 28 is connected to a flexible and compressible tubing 34. The other end of the tubing 34 is connected to the fluid supply arrangment 22. In this embodiment, the fluid supply 22 is defined by an opaque bottle 36 having a reservoir with a capacity adequate to retain an amount of fluid which allows completion of processing an entire roll of negative film. The fluid supply bottle 36 is removably supported in a vertical hold arrangement 38. In accordance with the present invention, the bottle 36 contains essentially an aqueous alkaline solution which is matched chemically to the sensitometry characteristics of the particular batch of film which is to be processed. This procedure, of course, optimizes the processing operation. In accordance with the present invention there is provided for each roll of film to be exposed and processed a bottle containing the correct amount of the matched processing fluid.

Reference is now made to the sensing assembly 26 which includes a magnetic sensor device 40 and a weighing sensor device 42 and a programmable controller unit 43. The controller unit 43 does not, per se, form an aspect of this invention. It includes appropriate circuitry to perform the functions set forth in the specification. The magnetic sensor 40 is spaced close to the advancing negative sheet 14 and it senses the presence of a magnetic medium, such as a magnetic strip 14a carried by the sheet 14. The distribution of the processing fluid is commenced when the magnetic sensing device senses a magnetic strip on the negative sheet 14. Of course, the magnetic strip precedes the exposed portion of the film. Once the magnetic strip is sensed the magnetic sensing device transmits a signal to the controller 43 which allows energization of the motor 44 to drive the pump 46, assuming the weighing sensor 42 also transmits a signal to the controller 43.

The pump 46 in this embodiment is of the peristaltic type and has a reversible rotating head assembly 48 carrying pins 481 which pins sequentially compress the tubing 34 and effect pumping of the fluid to the nozzle 28. The pump 46 has a retaining collar arrangement generally shown at 46' for insuring that the tubing 34 remains in contact with the pins of the head assembly 48 and is not pulled from the bottle 36. At the end of the exposed area, on the negative sheet 14 there is provided another magnetic strip (not shown) which is also sensed by the magnetic sensor device 40. The magnetic sensor device 40 is then operative because of the controller 43 to cause a reversal in the operation of the motor 44 such that pumping action of the pump 46 is also reversed. In other words, the fluid in the nozzle 28 and the tubing 34 is returned to the bottle 36, thereby evacuating the former of the easily oxidizable processing fluid. This is advantageous because the flow of fluid is terminated relatively quickly. Since the nozzle is evacuated the likelihood of fluid dripping from the nozzle is diminished significantly. This promotes cleanliness and safety when disposing the nozzle and reduces the likelihood of the sheets 12 and 14 sticking together.

Also not shown and not forming part of this invention, per se, there is a fluid monitoring assembly which includes a photoelectric assembly. The monitoring assembly is responsible for incrementing or decrementing the output of the pump as a function of the presence or absence of processing fluid in a reference area (not shown) adjacent the nip of the rollers so as to insure that processing fluid covers the exposed areas. Such a monitoring system can be similar to that described in copending and commonly assigned U.S. application Ser. No. 529,211 filed Sept. 6, 1983, now U.S. Pat. No. 4,526,455.

Referring back to the sensing assembly 26, it, as noted, includes the weight sensor device 42. Included in the weight sensor device 42 is commercially available check weighing unit 47 which is operatively connected to the controller 43. The holder 38 is affixed to a horizontal weighing platform 45 which holder and platform releasably holds and supports the bottle 36. The check weighing unit 47 is arranged to generate a signal to the controller 43 if the bottle 36 and fluid therein weigh at least a predetermined value. This value is indicative of the fact that there is sufficient fluid to process an entire roll of exposed negative film. The motor 44 will not be operative to cause operation of the pump 46 unless there is the predetermined amount of fluid. It is also contemplated that the entire processing operation including, for example, the advancement of the sheets 12, 14 be prevented from commencing. This is true even if the magnetic sensor 40 senses a strip on the sheet 14. The predetermined value is necessary to commence operation of the motor 44 for driving the pump 46 so that the fluid is dispersed from the nozzle 28. If the contents of the bottle 36 do not weigh the specified predetermined amount then the motor and pump assembly will not be operative for pumping purposes. Hence an operator will not be able to commence operation of a processing cycle unless a bottle 36, containing an adequate supply, is present to process an entire roll of exposed film.

This invention contemplates having the bottle 36 and the nozzle 28 and unexposed negative film roll packaged as one unit. Further, as noted the processing fluid in the bottle 36 is chemically matched to the sensiotimetric characteristics of the film for optimizing processing. Also in this regard, both the bottle 36 and nozzle 28 are intended to be disposable.

Since certain change may be made in the abovedescribed method and apparatus without departing from the scope of the invention herein involved, it is intended that all matter contained in the description or shown in the accompanying drawings shall be interpreted as illustrative and not in a limiting sense.

What is claimed is:

1. Apparatus for applying a coating of fluid initially retained in a container to an elongated section of a web of material,
   a fluid dispensing nozzle;
   means for progressively advancing the web of material along a predetermined path into operative relationship with said nozzle,
   weight sensing means for receiving the container;
   means for pumping the fluid from the container to said nozzle, said pumping means including a pump and a fluid line operatively associated with both said pump and said nozzle; and
   means for enabling said pump to be rendered operable only when the weight sensing means senses a weight indicative that an amount of fluid retained in the container is sufficient to cover the entire elongated section of the web.

2. The invention of claim 1 wherein said pump is a reversible pump and additionally including means for automatically reversing said pump responsive to the entire length of the elongated section of the web having been coated with the fluid thereby effecting an evacuation of at least a substantial portion of said fluid line and said nozzle.

3. The invention of claim 2 wherein the web of material is provided with a magnetic medium adjacent the trailing edge of its elongated section and said automatic reversing means includes a sensor positioned capable of detecting the presence of the magnetic medium.

4. The invention of claim 1 wherein the elongated section of the web of material comprises photographic material and the fluid is a film processing fluid, and additionally including means for progressively advancing another web of material along a path converging onto said predetermined path and into superposed overlying contact with the photographic material of the first-mentioned web, said nozzle serving to direct the fluid onto the elongated section of the first-mentioned web at a location adjacent the point of convergence between the two webs of material.

5. Apparatus for applying a coating of fluid initially retained in a container to an elongated section of a web of material, said apparatus comprising:
   a fluid dispensing nozzle;
   means for progressively advancing the web of material along a predetermined path into operative relationship with said nozzle;
   reversible means for pumping fluid from the container to said nozzle, said reversible pumping means including a reversible pump and a fluid line operably associated with said reversible pump and said nozzle; and
   means for automatically reversing said pump responsive to the entire length of the elongated sectional web having been coated with the fluid thereby effecting an evacuation of at least a substantial portion of said fluid line and said nozzle.

6. The invention of claim 5 wherein the web of material is provided with a magnetic medium adjacent the trailing edge of its elongated section and said automatic reversing means includes a sensor positioned adjacent said nozzle capable of detecting the presence of the magnetic medium.

7. The invention of claim 5 wherein the elongated section of the web of material comprises photographic material and the fluid is a film processing fluid, and additionally including means for progressively advancing another web of material along a path converging onto said predetermined path and into superposed overlying contact with the photographic material of the first-mentioned web, said nozzle serving to direct the fluid onto the elongated section of the first-mentioned web at a location adjacent the point of convergence between the two webs of material.

8. A method of applying a coating of a highly oxidizable fluid initially retained in a container to an elongated section of photographic film material comprising the steps of:
   advancing the film material along a predetermined path into operative relationship with a dispensing nozzle;
   pumping processing fluid through the nozzle to the film responsive to the container containing a sufficient amount of processing fluid to coat a preselected length of film;
   reversing the pumping action on the film so as to evacuate the nozzle responsive to coating of the preselected length of film,
   disposing the evacuated nozzle and replacing it with another dispensing nozzle.

9. A method of processing a plurality of individual rolls of photographic film separately, wherein each roll has different sensitometric characteristics comprising the steps of:
   providing processing fluid in containers, wherein each container has fluid matched chemically to sensitometric characteristics of respective ones of the film rolls;
   applying fluid from one of the containers, which fluid is matched to one of the rolls, through a nozzle to a preselected length of the one film roll to effect processing of the one film roll,
   evacuating the fluid from the nozzle after application of the fluid in the container; and,
   disposing the nozzle and the container following application of the fluid to the film roll and evacuation of the nozzle.

* * * * *